United States Patent [19]
Yates

[11] 4,061,022
[45] Dec. 6, 1977

[54] HAIR TESTING APPARATUS

[75] Inventor: Robert W. Yates, Woodland Hills, Calif.

[73] Assignee: Redken Laboratories, Inc., Van Nuys, Calif.

[21] Appl. No.: 706,631

[22] Filed: July 19, 1976

[51] Int. Cl.² .............................................. G01N 3/08
[52] U.S. Cl. .......................................................... 73/95
[58] Field of Search ................... 73/95, 95.5, 103, 160

[56] References Cited
U.S. PATENT DOCUMENTS

| 464,766 | 12/1891 | Wendler | 73/95 |
|---|---|---|---|
| 3,049,916 | 8/1962 | Weiner | 73/95 |
| 3,067,607 | 12/1962 | Crane et al. | 73/95 |
| 3,921,443 | 11/1975 | Yates | 73/95 |

Primary Examiner—Richard C. Queisser
Assistant Examiner—Anthony V. Ciarlante
Attorney, Agent, or Firm—Christie, Parker & Hale

[57] ABSTRACT

A tensile tester for hair strands in which the strand of hair is stretched between two movable members. The first member is supported from a frame by a pair of parallel flat springs, and the second member is cycled back and forth by an electric motor along a linear path extending perpendicular to the flat springs. The first member is locked between a stop and the second member in the initial position and is moved away from the stop by tension applied through the strand of hair as the second member is moved by the motor away from the initial position.

4 Claims, 5 Drawing Figures

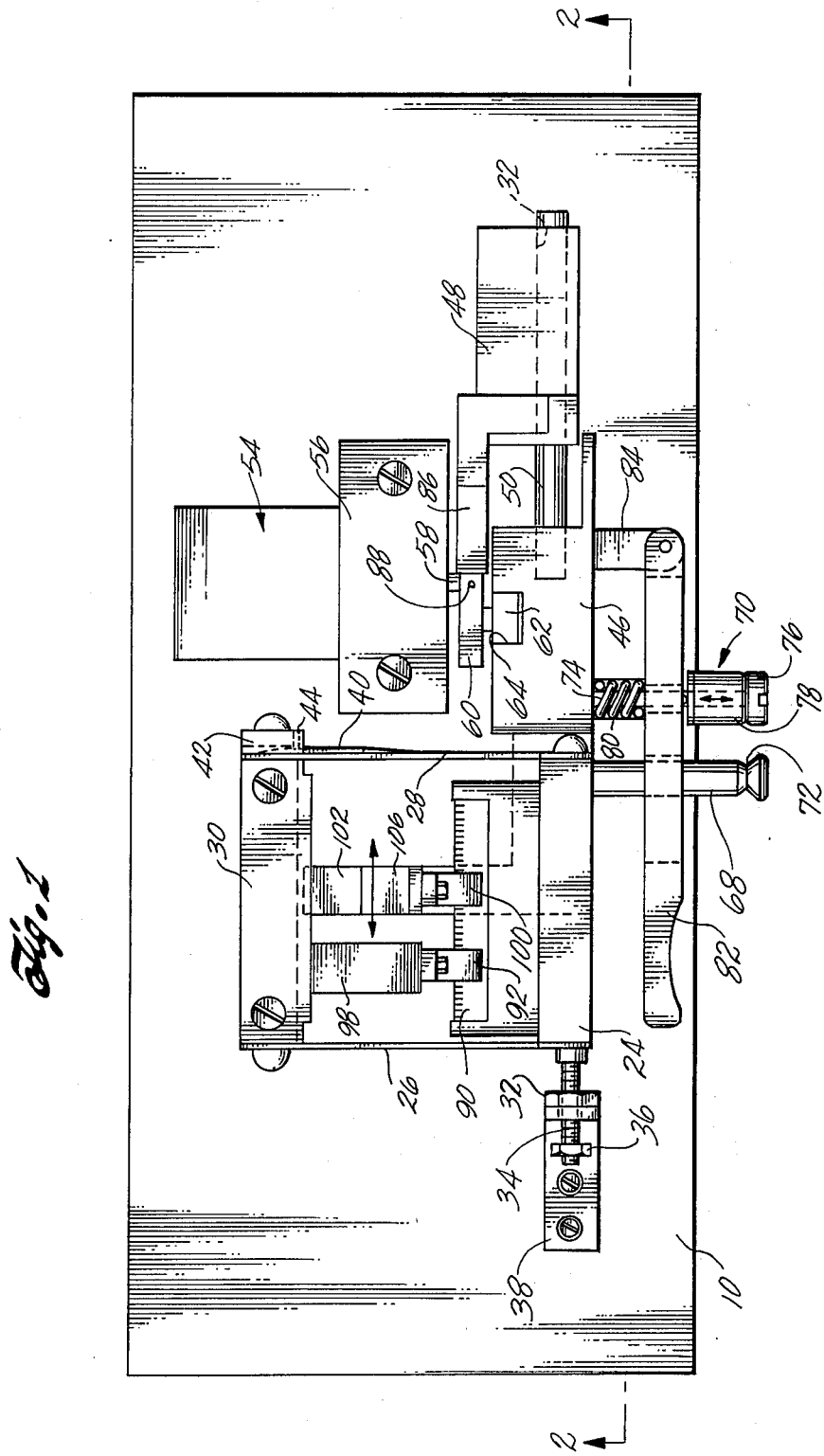

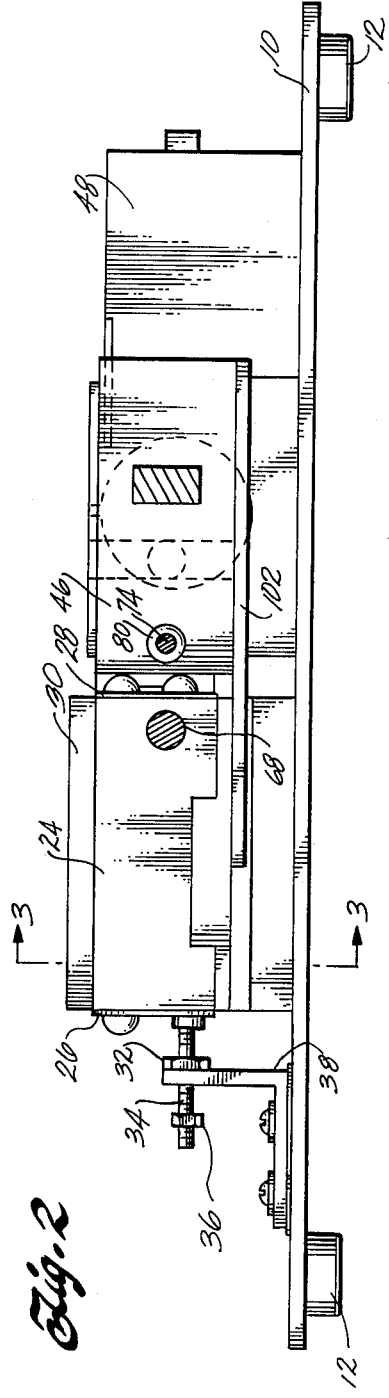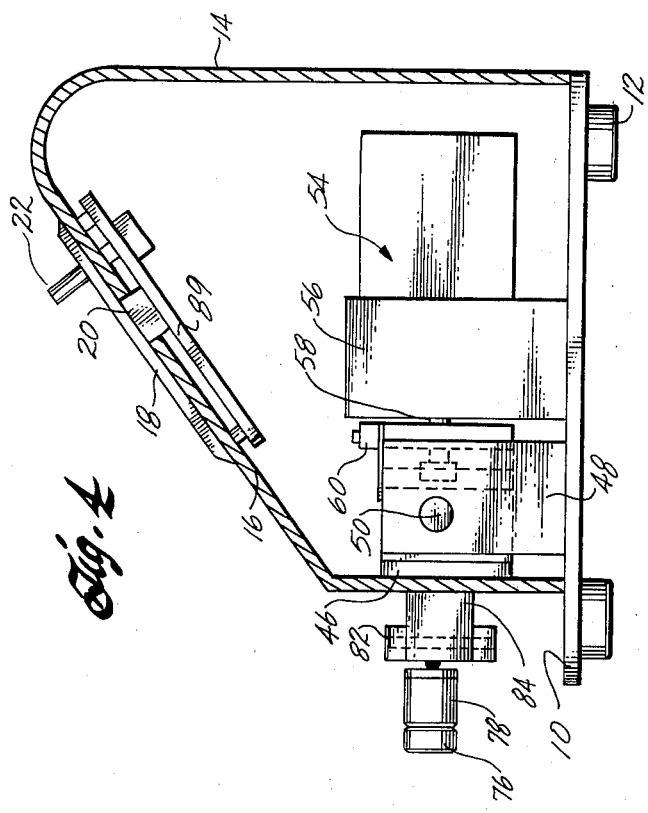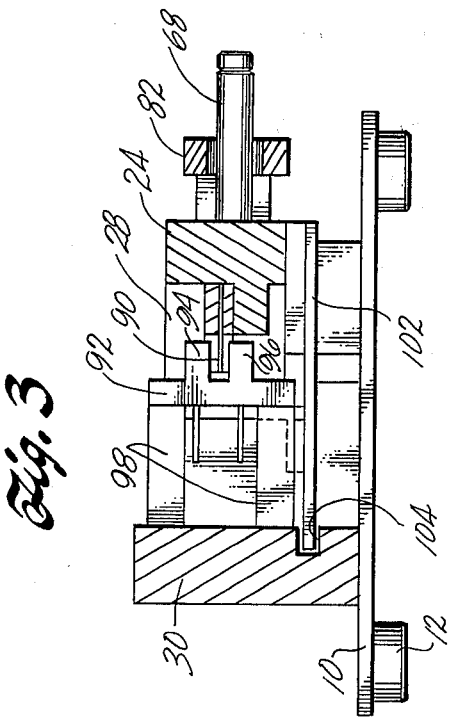

HAIR TESTING APPARATUS

FIELD OF THE INVENTION

This invention relates to a device for testing the tensile characteristics of human hair.

BACKGROUND OF THE INVENTION

In U.S. Pat. No. 3,921,443, assigned to the same assignee as the present invention, there is described a testing device for measuring the quality of human hair by placing the hair under tension and measuring the tensile force required to elongate the hair by a predetermined amount, namely, 10% elongation. The tester as described in the patent also measures the total elongation present when the hair is stretched to the breaking point. The present invention is directed to an improved tester of the type described in the above-identified patent. In particular, the present invention provides a tester which is simpler to operate, which is more easily calibrated, and provides more consistent results. The present invention provides a fully digitized system for detecting and indicating the tensile force and percentage elongation of the test sample.

SUMMARY OF THE INVENTION

In brief, the tester of the present invention incorporates first and second moving members with means for easily linking the two members by a sample strand of hair. The first moving member is supported from a base by a pair of cantilever flat springs extending parallel to each other. The springs act as a flexure support for the first moving member while at the same time providing a force which urges the first moving member against a stop. A second moving member is oscillated back and forth along a linear path extending perpendicular to the flat spring by an electric motor. Light sensors mounted respectively on the frame and on the second moving member sense the relative movement of the two moving members by a transparent scale mounted on the first moving member to provide a digitized indication of relative movement between the frame and the first moving member and between the two moving members.

DESCRIPTION OF THE DRAWINGS

For a better understanding of the invention reference should be made to the accompanying drawings, wherein:

FIG. 1 is a plan view of the hair testing unit of the present invention;

FIG. 2 is a sectional view taken on the line 2—2 of FIG. 1;

FIG. 3 is a sectional view taken on the line 3—3 of FIG. 2;

FIG. 4 is an end view of the tester unit; and

DETAILED DESCRIPTION

Figure 5:
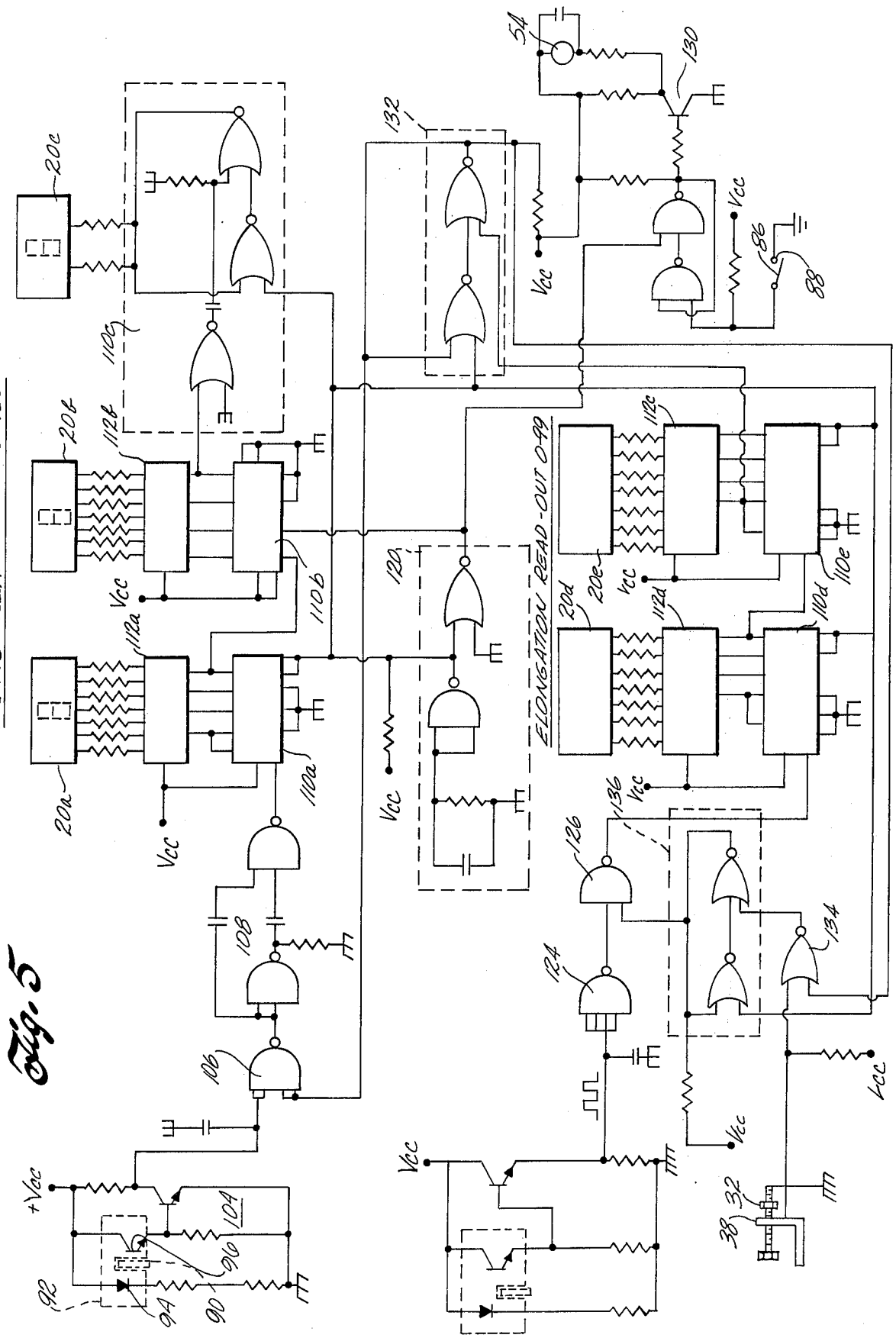
FIG. 5 is a schematic diagram of the electrical circuit.

Referring to the drawings in detail, the numeral 10 indicates generally the base plate or frame of the machine which preferably is supported on a flat surface by rubber feet 12 at each corner. A removable cover 14 fits over the frame plate, the cover 14 having a slanted front portion 16 on which is mounted a control panel 18. Light emitting diode type digital readout indicators 20 provide a visual display on the front of the panel 18 to indicate force and in grams and percentage elongation, in the manner hereinafter described in detail in connection with FIG. 5. An ON/OFF control switch 22 is mounted on the panel 18.

The testing apparatus includes a first movable member 24 preferably in the form of an elongated T-shaped bar. The first movable member is supported from the frame by a pair of flat springs 26 and 28 which are cantilever supported in spaced parallel relation from the frame 10 by a mounting block 30 which is bolted or otherwise secured to the frame 10. The horizontal length of the block 30 is the same as the length of the bar 24. One end of the springs 26 and 28 are secured respectively to the end faces of the block 30, while the other end is secured to the ends of the bar 24 to form a parallogram. The springs allow the bar to be displaced longitudinally along a linear path parallel to the base plate 10.

Movement of the bar 24 in one direction brings an adjustable stop in the form of a nut 32 into contact with a bracket 38. The nut 32 is supported by a screw 34 projecting from the bar 24 and movable therewith. The bracket 38 is electrically insulated from the base 10 so that when the nut 32 is moved by the bar 24 into contact with the bracket 38, the bracket is electrically grounded. The nut 32 and bracket 38 form switch contacts used in the electrical operation of the unit as described hereinafter in connection with the circuit diagram of FIG. 5.

The first moving member normally urges the nut 32 against bracket 38 by the springs 26 and 28. This force constitutes an initial preload condition which must be accurately adjusted to a known predetermined amount of force, e.g., 10 grams, by adjusting the nut 32 along the screw 34. A spring 40 is provided to adjust the deflection rate of the springs 26 and 28. The spring 40 is a leaf spring which is arcuate in shape and is held against the spring 28 adjacent one end by a clamping block 42. A set screw 44 in the clamping block 42 presses against the bias spring 40 to adjust the deflection of the bias spring. This in turn changes the deflection rate of the spring 28. A nonconductive nut 36 on the screw 34 limits overtravel that might damage the springs.

A second moving member 46 in the form of a metal block is positioned on the opposite side of the first moving member 24. The second moving member 46 is movably supported by means of a guide member preferably in the form of a Teflon block 48 mounted on the base plate 10. A guide rod 50 anchored at one end to the second moving member 46 slidably engages a hole 52 through the guide block 48 extending in a direction substantially perpendicular to the flat spring 26 and 28. The second moving member 46 and guide rod 50 are moved reciprocally relative to the guide block 48 by an electric motor drive, indicated generally at 54. The motor drive 54 has a gear head 56 and an output shaft 58. The shaft 58 rotates a disk 60. A roller 62 is mounted eccentrically on the disk 60, the roller 62 engaging a vertically extending slot 64 in the second moving member 46. As the motor rotates the disk 60, the roller 62 moves vertically in the slot 64 as it moves in a circular path around the axis of the shaft 58. Thus rotation of the motor 54 causes the second moving member 46 to oscillate back and forth along the axis of the guide rod 50. The member 46 is shown in its initial position in which it is normally at rest in its maximum extent of travel toward the first movable member 24. In this position, the first movable member is held against movement in either direction by the stop 32 at one end and by the second movable member 46 at the other end of the bar 24.

The hair strand under test is secured to the two moving members 24 and 46 by means of a post 68 projecting from the bar 24 and a clamping unit 70 secured to the moving member 46. The hair strand is formed in a loop which is slipped over the post 68 into a notch 72. The two ends of the loop are gripped by the clamping unit 70. The clamping unit includes a screw 74 which threadedly engages the second moving member 46 and terminates in a head 76. This screw slidably supports a clamping sleeve 78, the strands of hair being clamped between the inside of the head 76 and the end of the sleeve 78. A coil spring 80 is positioned between a clamp release lever 82 and the second moving member 46 along the screw 74. The clamp lever 82 is pivotally attached at one end to a supporting lug 84 projecting from the second moving member 46. The screw 74 passes through a hole in the clamp lever 82. By pressing in on the free end of the clamp lever 82, the coil spring 80 is compressed thereby relieving the clamping pressure from the sleeve 78 and permitting the ends of the hair strand to be slipped in between the clamping surfaces formed by the end of the sleeve 78 and the screw head 76. The lever 82 is then released, causing the loop of hair to be clamped in position in a loop around the post 68.

With the hair strand looped and clamped in place in the manner described, the motor 54 is energized by actuating the control switch 22, causing the second moving member 46 to move initially to the right as viewed in FIG. 1, thereby putting the hair strand under tension. When the tension in the hair strand reaches a predetermined level set by the adjustment of the spring 40, it will pull the first moving member 24 off the stop 32. As the second moving member continues to move to the right, the springs 26 and 28 exert an ever increasing tension on the hair strand, causing the hair strand to stretch until it breaks. The motor continues to run until the disk 60 makes a complete revolution, returning the second moving member 46 back to its initial position. A switch contact 86 projecting from the Teflon guide block 48 is contacted by a pin 88 on the periphery of the disk 60, thereby momentarily completing an electrical circuit which operates to automatically stop the motor 54 when the disk 60 has completed one revolution.

Operation of the measurement cycle and the measurement of force and elongation are provided by an electrical circuit mounted inside the cover, as indicated at 89. Tensile force is measured by sensing the deflection of the first moving member 24 relative to the base plate 10, while the percentage elongation is measured by sensing the displacement of the second moving member 46 relative to the first moving member 24.

Referring to FIGS. 1-4, displacement of the first moving member 24 relative to the base plate 10 is measured by means of a scale element 90 in the form of a transparent film on which a scale consisting of a series of equally spaced opaque lines or indicia are separated by transparent spaces. The scale element 90 is mounted along the inside of the bar 24 so that the indicia of the scale are displaced relative to the base 10 by movement of the bar 24 away from the stop 32. The scale element 90 moves through an optical sensor 92 which includes a light emitting diode 94 positioned on one side of the scale 90 and a light sensitive transistor 96 on the opposite side of the scale. The optical sensor 92 is rigidly supported from the block 30 by a pair of support arms 98. As the lines of the scale move past the light sensor, the light is chopped by the indicia of the scale, generating a corresponding series of electrical pulses from the light sensitive transistor 96. By counting the number of these pulses, in a manner hereinafter described, an indication of the amount of relative displacement between the scale and the fixed position of the light sensor can be ascertained.

A second light sensor element 100 is positioned along the scale 90 and is supported in fixed relation with the second movable member 46. To this end, an L-shaped supporting plate 102 has one leg thereof secured to the underside of the second movable member 46 and extends below the first movable member 24. The other leg of the L-shaped plate 102 extends toward the block 30 and terminates in sliding contact with a slot 104 in the block 30. A bracket 106 supports the optical sensor element 100 from the plate 102. Relative movement between the two moving members 24 and 46 causes the scale 90 to chop the light sensor beam of the sensor unit 100, generating a series of pulses, the number of which is indicative of the degree of relative movement between the two moving members.

Referring in detail to the circuit diagram of FIG. 5, the digital readout for the force in grams is indicated generally at 20 and includes three digit displays 20a, 20b, and 20c. Each digit display is a standard seven element LED display by means of which each of the digital characters 0 through 9 can be visually formed. The display elements are controlled by counters 110a, 110b and 110c and decoder drivers 112a and 112b. However, since the highest order digit 20c displays only a 0 or a 1, a full counter and driver is not required. Similarly, the elongation readout includes a pair of digital display elements 20e and 20d controlled by counters 110d and 110e which control the display through decode drivers 112d and 112e.

The force counter and digital display is operated in response to the optical detector 92 by means of a conventional light amplifier circuit 104 which generates amplified output pulses in response to movement of the alternate transparent and opaque indicia of the scale 90 past the sensor 92. These pulses are applied to one input of a Schmidt trigger 106. The output of the Schmidt trigger 106 is applied through a pulse doubler circuit 108 to the input of the counter 110a. The spacing of the indicia on the scale 90 is such that a displacement distance produced by one gram of force on the moving member 24 advances the counter by one count, so that the digital readout indicates the tension force directly in units of grams. Moreover the second stage counter 110b is initially set to a count of one so that the digital display indicates intitially 10 gram. This is the force required to move the first movable member 24 off the stop provided by contact of the nut 32 with the bracket 38 as accurately set by the position of the nut 32. An automatic reset circuit 120 applies a reset signal to the counters when the supply voltage Vcc is turned on at the start of a measurement cycle. The reset circuit sets all the counter stages to 0 except stage 110b, which is set to 1.

Similarly the elongation readout is controlled by the optical sensor 100 by means of a light amplifier circuit 122 which produces output pulses as the indicia of the scale 90 are scanned by the sensor 100. These pulses are shaped by means of a Schmidt trigger 124 and coupled through a gate 126 into the input of the counter stage 110d.

The motor 54 is controlled by a power transistor 130 which is switched on by the automatic reset circuit 120. The motor continues to run until the transistor 130 is turned off by the momentary grounding of the switch contact 86 and the pin 88, as described in connection with FIG. 1. The motor cannot be turned on again until the supply voltage Vcc is turned off by switch 22 and again turned on.

The tension force is measured at the yield point of the hair which typically is in the neighborhood of a 10% elongation. To this end, an output is derived from the counter 110e which is applied to one input of a trigger circuit 132. When the elongation counter 110e reaches a count corresponding to an elongation of 10%, the trigger circuit 132 provides an output which turns off the Schmidt trigger circuit 106, preventing further counting of the force counter stages 110a, 110b, and 110c. Thus counting is interrupted at the force level corresponding to a 10% elongation of the hair under test. The trigger circuit 132 is reset by the automatic reset circuit 120.

The elongation counter continues to count until the hair breaks. It is described to lock the elongation counter at the count condition pertaining when the hair breaks. This condition is sensed by the switch formed by the nut 32 making contact with the angle bracket 38. When the moving member 24 is released by the breaking of the hair linking the first and second moving members, the output of the trigger circuit 132 together with the positive voltage from the supply Vcc is applied to the inputs of a gate 134. The output of the gate 134 goes true only if both inputs go to zero, which condition only applies if the elongation reading exceeds 10% and the bracket 38 is connected to ground by the contact with the nut 32 and through the spring 26. The output of the gate 134 operates a trigger circuit at 136 which in turn controls a second input to the gate 126 to turn off the gate 126 and stop further counting. The trigger circuit 136 is reset by the automatic reset circuit 120 at the start of a new measuring cycle.

From the above description it will be seen that a digitized fully automatic measuring system is provided for quickly and accurately measuring the tension force required to stretch a strand of hair to the yield point (10% elongation) and to measure the percent elongation required to reach the breaking point of the hair. The device automatically resets itself at the end of each measurement cycle. The digital readout is held on the display until a new measurement cycle is initiated.

One of the features of the invention is the spring system which supports the moving member 24. The parallel springs 26 and 28 are the only contact between the moving member and the rest of the structure so that no friction or other extraneous loads are imposed on the hair through the moving member 24. This results in much greater accuracy and stability with continued use over a long period of time.

What is claimed is:

1. A tensile tester for strands of hair comprising a frame, a first movable member, a pair of parallel flat springs secured at one end to the first movable member and anchored at the other end to the frame for movably supporting the first member from the frame, a second movable member, means for driving the second member relative to the frame in a continuous uninterrupted cycle along a predetermined linear path extending substantially perpendicular to said flat springs from an initial position through a fixed displacement away from the first member and return to the initial position, means for securing a hair sample to the two movable members, a stop mounted on the frame and engaging the first movable member in an initial position, the flat springs urging the first movable member against the stop, a scale member mounted on the first movable member having a plurality of equally spaced indicia extending therealong, the indicia being spaced along a direction parallel to the direction of movement of the first member, first counting means including a first sensor mounted on the frame for counting the number of indicia passing the sensor with movement of the first member, and means responsive to said first counting means for generating a digital output of the number of indicia sensed by the first sensor, second counting means including a second sensor mounted on the second movable member for counting the number of indicia passing the second sensor with relative movement between the first and second movable members, and means responsive to said last-named means for generating a second digital output of the number of indicia sensed by the second sensor.

2. Apparatus of claim 1 futher including a first post projecting from the first member, a second post projecting from the second member, a flange on the outer end of the second post, a clamping member slidable on the post into engagement with the flange, spring means urging the clamping member against the flange, and a release lever operable to release the pressure of the spring means to permit a hair sample to be inserted between the flange and the clamping member.

3. Apparatus of claim 1 further including means responsive to the second counting means for interrupting the first counting means when the second counting means reaches a predetermined count condition.

4. Apparatus of claim 3 including means for interrupting the second counting means when the first movable member reengages said stop.

* * * * *